United States Patent
Mast et al.

(10) Patent No.: US 7,846,096 B2
(45) Date of Patent: *Dec. 7, 2010

(54) METHOD FOR MONITORING OF MEDICAL TREATMENT USING PULSE-ECHO ULTRASOUND

(75) Inventors: T. Douglas Mast, Cincinnati, OH (US); Waseem Faidi, Clifton Park, NY (US); Inder Raj S. Makin, Loveland, OH (US); Peter G. Barthe, Phoenix, AZ (US); Michael H. Slayton, Tempe, AZ (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/721,034

(22) Filed: Nov. 24, 2003

(65) Prior Publication Data

US 2004/0106870 A1 Jun. 3, 2004

Related U.S. Application Data

(63) Continuation-in-part of application No. 10/153,241, filed on May 22, 2002, now abandoned.

(60) Provisional application No. 60/294,135, filed on May 29, 2001.

(51) Int. Cl.
*A61B 8/00* (2006.01)
(52) U.S. Cl. .................. 600/437; 600/407; 600/439; 601/2; 601/3; 601/4
(58) Field of Classification Search ......... 600/437–439, 600/443, 447, 407; 601/2–4; 606/1; 604/22; 374/117
See application file for complete search history.

(56) References Cited

U.S. PATENT DOCUMENTS 3,168,659 A 2/1965 Bayre et al.

(Continued)

FOREIGN PATENT DOCUMENTS

EP 0897696 2/1999

(Continued)

OTHER PUBLICATIONS

International Preliminary Examination Report dated Mar. 30, 2004 for corresponding International patent application No. PCT/US02/16695.

(Continued)

*Primary Examiner*—Brian Casler
*Assistant Examiner*—Baisakhi Roy
(74) *Attorney, Agent, or Firm*—Verne E. Kreger, Jr.

(57) ABSTRACT

A method for ultrasound imaging of anatomical tissue. A first signal is received from a first imaging ultrasound wave which has been reflected from a location in the anatomical tissue during a first time period. A second signal is received from a second imaging ultrasound wave which has been reflected from the location in the anatomical tissue during a later second time period, following a discrete medical treatment. The second signal is subtracted from the first signal to form a difference signal. The difference signal may be scaled, spatially filtered, then used to generate an indication, the indication showing the effect of the medical treatment in the location in the anatomical tissue.

32 Claims, 10 Drawing Sheets

U.S. PATENT DOCUMENTS

| | | |
|---|---|---|
| 3,779,234 A | 12/1973 | Eggleton et al. |
| 3,902,501 A | 9/1975 | Citron et al. |
| 3,927,557 A | 12/1975 | Viertl |
| 4,211,948 A | 7/1980 | Smith et al. |
| 4,315,514 A | 2/1982 | Drewes et al. |
| 4,323,077 A | 4/1982 | Smith |
| 4,484,569 A | 11/1984 | Driller et al. |
| 4,646,756 A | 3/1987 | Watmough et al. |
| 4,748,985 A | 6/1988 | Nagasaki |
| 4,757,820 A | 7/1988 | Itoh |
| 4,787,394 A | 11/1988 | Ogura |
| 4,790,329 A | 12/1988 | Simon |
| 4,798,215 A | 1/1989 | Turner |
| 4,818,954 A | 4/1989 | Flachenecker et al. |
| 4,844,080 A | 7/1989 | Frass et al. |
| 4,858,613 A | 8/1989 | Fry et al. |
| 4,932,414 A | 6/1990 | Coleman et al. |
| 4,937,767 A | 6/1990 | Reuschel et al. |
| 4,951,653 A | 8/1990 | Fry et al. |
| 4,955,365 A | 9/1990 | Fry et al. |
| 4,955,366 A | 9/1990 | Uchiyama et al. |
| 4,960,107 A | 10/1990 | Aida et al. |
| 4,960,109 A | 10/1990 | Lele |
| 4,984,575 A | 1/1991 | Uchiyama et al. |
| 4,986,275 A | 1/1991 | Ishida et al. |
| 5,005,580 A * | 4/1991 | Okazaki ............... 600/439 |
| RE33,590 E | 5/1991 | Dory |
| 5,015,929 A | 5/1991 | Cathignol et al. |
| 5,031,626 A | 7/1991 | Hassler et al. |
| 5,036,855 A | 8/1991 | Fry et al. |
| 5,042,486 A | 8/1991 | Pfeiler et al. |
| 5,054,470 A | 10/1991 | Fry et al. |
| 5,065,740 A | 11/1991 | Itoh |
| 5,078,144 A | 1/1992 | Sekino et al. |
| 5,080,101 A | 1/1992 | Dory |
| 5,080,102 A | 1/1992 | Dory |
| 5,095,906 A * | 3/1992 | Ema ............... 600/407 |
| 5,095,907 A | 3/1992 | Kudo et al. |
| 5,117,832 A | 6/1992 | Sanghvi et al. |
| 5,143,073 A | 9/1992 | Dory |
| 5,143,074 A | 9/1992 | Dory |
| 5,148,809 A * | 9/1992 | Biegeleisen-Knight et al. ............... 600/443 |
| 5,149,319 A | 9/1992 | Unger |
| 5,150,711 A * | 9/1992 | Dory ............... 600/439 |
| 5,150,712 A | 9/1992 | Dory |
| 5,158,070 A | 10/1992 | Dory |
| 5,158,071 A | 10/1992 | Umemura et al. |
| 5,203,333 A | 4/1993 | Nomura |
| 5,209,221 A | 5/1993 | Riedlinger |
| 5,238,007 A | 8/1993 | Giele et al. |
| 5,240,005 A | 8/1993 | Viebach |
| 5,242,437 A | 9/1993 | Everett et al. |
| 5,295,484 A | 3/1994 | Marcus et al. |
| 5,304,115 A | 4/1994 | Pflueger et al. |
| 5,311,869 A | 5/1994 | Okazaki |
| 5,345,940 A | 9/1994 | Seward et al. |
| 5,348,017 A | 9/1994 | Thornton et al. |
| 5,354,258 A * | 10/1994 | Dory ............... 601/3 |
| 5,370,121 A * | 12/1994 | Reichenberger et al. .... 600/438 |
| 5,391,140 A | 2/1995 | Schaetzle et al. |
| 5,391,197 A | 2/1995 | Burdette et al. |
| 5,398,690 A | 3/1995 | Batten et al. |
| 5,398,691 A | 3/1995 | Martin et al. |
| 5,402,792 A | 4/1995 | Kimura |
| 5,409,002 A | 4/1995 | Pell |
| 5,419,335 A | 5/1995 | Hartmann et al. |
| 5,421,338 A | 6/1995 | Crowley et al. |
| 5,431,663 A | 7/1995 | Carter |
| 5,435,304 A | 7/1995 | Oppelt et al. |
| 5,435,311 A | 7/1995 | Umemura et al. |
| 5,443,069 A | 8/1995 | Schaetzle |
| 5,448,994 A | 9/1995 | Iinuma |
| 5,458,597 A | 10/1995 | Edwards et al. |
| 5,465,724 A | 11/1995 | Sliwa et al. |
| 5,471,988 A | 12/1995 | Fujio et al. |
| 5,474,071 A | 12/1995 | Chapelon et al. |
| 5,485,839 A | 1/1996 | Aida et al. |
| 5,492,126 A | 2/1996 | Hennige et al. |
| 5,500,012 A | 3/1996 | Brucker et al. |
| 5,501,655 A | 3/1996 | Rolt et al. |
| 5,514,085 A | 5/1996 | Yoon |
| 5,514,130 A | 5/1996 | Baker |
| 5,520,188 A | 5/1996 | Hennige et al. |
| 5,522,869 A | 6/1996 | Burdette et al. |
| 5,524,620 A | 6/1996 | Rosenschein |
| 5,526,815 A | 6/1996 | Granz et al. |
| 5,526,816 A * | 6/1996 | Arditi ............... 600/458 |
| 5,526,822 A | 6/1996 | Burbank et al. |
| 5,540,656 A | 7/1996 | Pflueger et al. |
| 5,545,195 A | 8/1996 | Lennox et al. |
| 5,547,459 A | 8/1996 | Kaufman et al. |
| 5,549,638 A | 8/1996 | Burdette |
| 5,553,618 A | 9/1996 | Suzuki et al. |
| 5,558,092 A | 9/1996 | Unger et al. |
| 5,569,241 A | 10/1996 | Edwards |
| 5,571,088 A | 11/1996 | Lennox et al. |
| 5,573,497 A | 11/1996 | Chapelon |
| 5,575,288 A | 11/1996 | Sliwa et al. |
| 5,575,772 A | 11/1996 | Lennox |
| 5,575,789 A | 11/1996 | Bell et al. |
| 5,582,588 A | 12/1996 | Sakurai et al. |
| 5,588,432 A | 12/1996 | Crowley |
| 5,590,657 A | 1/1997 | Cain et al. |
| 5,596,991 A | 1/1997 | Tanaka |
| 5,601,526 A | 2/1997 | Chapelon et al. |
| 5,603,326 A | 2/1997 | Richter |
| 5,606,975 A | 3/1997 | Liang et al. |
| 5,620,479 A | 4/1997 | Diederich |
| 5,624,382 A | 4/1997 | Oppelt et al. |
| 5,626,607 A | 5/1997 | Malecki et al. |
| 5,628,743 A | 5/1997 | Cimino |
| 5,630,837 A | 5/1997 | Crowley |
| 5,643,179 A | 7/1997 | Fujimoto |
| 5,649,547 A | 7/1997 | Ritchart et al. |
| 5,657,760 A | 8/1997 | Ying et al. |
| 5,665,054 A | 9/1997 | Dory |
| 5,666,954 A | 9/1997 | Chapelon et al. |
| 5,676,692 A | 10/1997 | Sanghvi et al. |
| 5,687,729 A | 11/1997 | Schaetzle |
| 5,694,936 A | 12/1997 | Fujimoto et al. |
| 5,697,897 A | 12/1997 | Buchholtz et al. |
| 5,699,804 A | 12/1997 | Rattner |
| 5,699,805 A | 12/1997 | Seward et al. |
| 5,703,922 A | 12/1997 | Rattner |
| 5,715,825 A | 2/1998 | Crowley |
| 5,720,287 A | 2/1998 | Chapelon et al. |
| 5,722,411 A | 3/1998 | Suzuki et al. |
| 5,728,062 A | 3/1998 | Brisken |
| 5,733,315 A | 3/1998 | Burdette et al. |
| 5,735,280 A | 4/1998 | Sherman et al. |
| 5,735,796 A | 4/1998 | Granz et al. |
| 5,738,635 A | 4/1998 | Chapelon et al. |
| 5,743,862 A | 4/1998 | Izumi |
| 5,743,863 A | 4/1998 | Chapelon |
| 5,746,224 A | 5/1998 | Edwards |
| 5,759,154 A | 6/1998 | Hoyns |
| 5,759,162 A | 6/1998 | Oppelt et al. |
| 5,762,066 A | 6/1998 | Law et al. |
| 5,769,086 A | 6/1998 | Ritchart et al. |
| 5,769,790 A * | 6/1998 | Watkins et al. ............... 600/439 |
| 5,771,896 A | 6/1998 | Sliwa et al. |
| 5,776,092 A | 7/1998 | Farin et al. |
| 5,779,643 A | 7/1998 | Lum et al. |

| Patent No. | Date | Inventor |
|---|---|---|
| 5,782,764 A | 7/1998 | Werne |
| 5,785,705 A | 7/1998 | Baker |
| 5,788,636 A | 8/1998 | Curley |
| 5,800,379 A | 9/1998 | Edwards |
| 5,807,308 A | 9/1998 | Edwards |
| 5,810,742 A | 9/1998 | Pearlman |
| 5,817,021 A | 10/1998 | Reichenberger |
| 5,817,049 A | 10/1998 | Edwards |
| 5,820,580 A | 10/1998 | Edwards et al. |
| 5,823,962 A | 10/1998 | Schaetzle et al. |
| 5,836,896 A | 11/1998 | Rosenschein |
| 5,840,022 A | 11/1998 | Richter |
| 5,840,031 A | 11/1998 | Crowley |
| 5,860,974 A | 1/1999 | Abele |
| 5,873,828 A | 2/1999 | Fujio et al. |
| 5,873,845 A | 2/1999 | Cline et al. |
| 5,873,902 A | 2/1999 | Sanghvi et al. |
| 5,876,399 A | 3/1999 | Chia et al. |
| 5,882,302 A | 3/1999 | Driscoll, Jr. et al. |
| 5,893,835 A | 4/1999 | Witt et al. |
| 5,895,356 A | 4/1999 | Andrus et al. |
| 5,897,495 A | 4/1999 | Aida et al. |
| 5,906,580 A | 5/1999 | Kline-Schoder et al. |
| 5,928,169 A | 7/1999 | Schatzle et al. |
| 5,931,805 A | 8/1999 | Brisken |
| 5,931,848 A | 8/1999 | Saadat |
| 5,938,600 A | 8/1999 | Van Vaals et al. |
| 5,938,608 A | 8/1999 | Bieger et al. |
| 5,944,663 A | 8/1999 | Kuth et al. |
| 5,964,755 A | 10/1999 | Edwards |
| 5,976,105 A | 11/1999 | Marcove et al. |
| 5,979,453 A | 11/1999 | Savage et al. |
| 5,984,881 A | 11/1999 | Ishibashi et al. |
| 5,984,882 A | 11/1999 | Rosenschein et al. |
| 5,987,523 A | 11/1999 | Hind et al. |
| 5,993,389 A | 11/1999 | Driscoll, Jr. et al. |
| 5,997,534 A | 12/1999 | Tu et al. |
| 6,001,069 A | 12/1999 | Tachibana et al. |
| 6,004,269 A | 12/1999 | Crowley et al. |
| 6,007,499 A | 12/1999 | Martin et al. |
| 6,010,531 A | 1/2000 | Donlon et al. |
| 6,013,031 A | 1/2000 | Mendlein et al. |
| 6,022,319 A | 2/2000 | Willard et al. |
| 6,024,718 A | 2/2000 | Chen et al. |
| 6,024,740 A | 2/2000 | Lesh et al. |
| 6,030,344 A * | 2/2000 | Guracar et al. ............. 600/447 |
| 6,039,689 A | 3/2000 | Lizzi |
| 6,042,556 A | 3/2000 | Beach et al. |
| 6,050,943 A | 4/2000 | Slayton et al. |
| 6,053,868 A | 4/2000 | Geistert et al. |
| 6,059,731 A | 5/2000 | Seward et al. |
| 6,063,050 A | 5/2000 | Manna et al. |
| 6,066,123 A | 5/2000 | Li et al. |
| 6,071,238 A | 6/2000 | Chapelon et al. |
| 6,071,239 A | 6/2000 | Cribbs et al. |
| 6,071,279 A | 6/2000 | Whayne et al. |
| 6,083,159 A | 7/2000 | Driscoll et al. |
| 6,086,535 A | 7/2000 | Ishibashi et al. |
| 6,086,539 A * | 7/2000 | Guracar et al. ............. 600/453 |
| 6,088,613 A | 7/2000 | Unger |
| 6,093,149 A * | 7/2000 | Guracar et al. ............. 600/447 |
| 6,106,470 A * | 8/2000 | Geiser et al. ............. 600/443 |
| 6,106,517 A | 8/2000 | Zupkas |
| 6,110,118 A * | 8/2000 | Guracar et al. ............. 600/453 |
| 6,112,123 A | 8/2000 | Kelleher et al. |
| 6,113,558 A | 9/2000 | Rosenschein et al. |
| 6,117,101 A | 9/2000 | Diederich et al. |
| 6,128,958 A | 10/2000 | Cain |
| 6,135,963 A | 10/2000 | Haider |
| 6,135,971 A | 10/2000 | Hutchinson et al. |
| 6,138,513 A | 10/2000 | Barabash et al. |
| 6,149,598 A | 11/2000 | Tanaka |
| 6,156,029 A | 12/2000 | Mueller |
| 6,159,207 A | 12/2000 | Yoon |
| 6,171,248 B1 | 1/2001 | Hossack et al. |
| 6,176,842 B1 | 1/2001 | Tachibana et al. |
| 6,183,469 B1 | 2/2001 | Thapliyal et al. |
| 6,193,664 B1 * | 2/2001 | Guracar et al. ............. 600/453 |
| 6,193,709 B1 | 2/2001 | Miyawaki et al. |
| 6,206,843 B1 | 3/2001 | Iger et al. |
| 6,210,330 B1 | 4/2001 | Tepper |
| 6,216,704 B1 | 4/2001 | Ingle et al. |
| 6,217,576 B1 | 4/2001 | Tu et al. |
| 6,221,014 B1 | 4/2001 | Bauer |
| 6,231,834 B1 | 5/2001 | Unger et al. |
| 6,241,677 B1 * | 6/2001 | Guracar et al. ............. 600/453 |
| 6,246,898 B1 | 6/2001 | Vesely et al. |
| 6,258,029 B1 * | 7/2001 | Guracar et al. ............. 600/443 |
| 6,266,552 B1 | 7/2001 | Slettenmark |
| 6,315,723 B1 * | 11/2001 | Robinson et al. ............. 600/443 |
| 6,322,511 B1 * | 11/2001 | Guracar et al. ............. 600/453 |
| 6,340,348 B1 | 1/2002 | Krishnan et al. |
| 6,340,352 B1 | 1/2002 | Okada et al. |
| 6,352,532 B1 | 3/2002 | Kramer et al. |
| 6,361,531 B1 | 3/2002 | Hissong |
| 6,371,903 B1 | 4/2002 | Blanc et al. |
| 6,371,973 B1 | 4/2002 | Tepper |
| 6,379,320 B1 | 4/2002 | Lafon et al. |
| 6,425,867 B1 | 7/2002 | Vaezy et al. |
| 6,428,477 B1 | 8/2002 | Mason |
| 6,440,147 B1 | 8/2002 | Lee et al. |
| 6,461,314 B1 | 10/2002 | Pant et al. |
| 6,464,640 B1 * | 10/2002 | Guracar et al. ............. 600/453 |
| 6,482,178 B1 | 11/2002 | Andrews et al. |
| 6,488,626 B1 | 12/2002 | Lizzi et al. |
| 6,488,630 B1 | 12/2002 | Hand et al. |
| 6,508,774 B1 * | 1/2003 | Acker et al. ............. 601/2 |
| 6,512,957 B1 | 1/2003 | Witte |
| 6,521,211 B1 | 2/2003 | Unger et al. |
| 6,533,726 B1 * | 3/2003 | Lizzi et al. ............. 600/439 |
| 6,540,700 B1 * | 4/2003 | Fujimoto et al. ............. 601/3 |
| 6,546,934 B1 | 4/2003 | Ingle et al. |
| 6,562,033 B2 | 5/2003 | Shah et al. |
| 6,575,969 B1 | 6/2003 | Rittman et al. |
| 6,599,245 B1 | 7/2003 | Ma et al. |
| 6,602,251 B2 | 8/2003 | Burbank et al. |
| 6,613,004 B1 | 9/2003 | Vitek et al. |
| 6,618,620 B1 | 9/2003 | Freundlich et al. |
| 6,626,855 B1 | 9/2003 | Weng et al. |
| 6,635,054 B2 | 10/2003 | Fjield et al. |
| 6,638,235 B2 | 10/2003 | Miller et al. |
| 6,641,579 B1 | 11/2003 | Bernardi et al. |
| 6,645,202 B1 | 11/2003 | Pless et al. |
| 6,659,949 B1 | 12/2003 | Lang et al. |
| 6,669,638 B1 | 12/2003 | Miller et al. |
| 6,673,019 B2 * | 1/2004 | Kamiyama ............. 600/443 |
| 6,682,483 B1 | 1/2004 | Abend et al. |
| 6,702,745 B1 | 3/2004 | Smythe |
| 6,716,184 B2 | 4/2004 | Vaezy et al. |
| 6,719,694 B2 | 4/2004 | Weng et al. |
| 6,726,677 B1 | 4/2004 | Flaherty et al. |
| 6,764,488 B1 | 7/2004 | Burbank et al. |
| 6,770,070 B1 | 8/2004 | Balbierz |
| 6,887,239 B2 | 5/2005 | Elstrom et al. |
| 6,902,536 B2 | 6/2005 | Manna et al. |
| 6,921,371 B2 | 7/2005 | Wilson |
| 6,936,024 B2 | 8/2005 | Houser |
| 6,936,048 B2 | 8/2005 | Hurst |
| 6,974,417 B2 | 12/2005 | Lockwood et al. |
| 7,035,166 B2 | 4/2006 | Zimmerman et al. |
| 7,037,306 B2 | 5/2006 | Podany et al. |
| 7,063,666 B2 | 6/2006 | Weng et al. |
| 7,078,015 B2 | 7/2006 | Unger |
| 7,410,469 B1 * | 8/2008 | Talish et al. ............. 601/2 |
| 2001/0007940 A1 | 7/2001 | Tu et al. |
| 2001/0014805 A1 | 8/2001 | Burbank et al. |

| | | |
|---|---|---|
| 2001/0037073 A1 | 11/2001 | White et al. |
| 2002/0065512 A1 | 5/2002 | Fjield et al. |
| 2002/0068934 A1 | 6/2002 | Edwards et al. |
| 2002/0087081 A1 | 7/2002 | Serrano et al. |
| 2002/0087803 A1 | 7/2002 | Jones et al. |
| 2002/0111662 A1 | 8/2002 | Iaizzo et al. |
| 2002/0165579 A1 | 11/2002 | Burbank et al. |
| 2002/0183371 A1 | 12/2002 | Gordeev et al. |
| 2002/0183742 A1 | 12/2002 | Carmel et al. |
| 2002/0193731 A1 | 12/2002 | Myers et al. |
| 2003/0004434 A1 | 1/2003 | Greco et al. |
| 2003/0013960 A1 | 1/2003 | Makin et al. |
| 2003/0013971 A1 | 1/2003 | Makin et al. |
| 2003/0014093 A1 | 1/2003 | Makin |
| 2003/0018266 A1 | 1/2003 | Makin et al. |
| 2003/0018358 A1 | 1/2003 | Saadat |
| 2003/0028111 A1 | 2/2003 | Vaezy et al. |
| 2003/0040698 A1 | 2/2003 | Makin et al. |
| 2003/0047582 A1 | 3/2003 | Sonnenschein et al. |
| 2003/0073907 A1 | 4/2003 | Taylor |
| 2003/0109786 A1 | 6/2003 | Irioka et al. |
| 2003/0120270 A1 | 6/2003 | Acker |
| 2003/0120306 A1 | 6/2003 | Burbank et al. |
| 2003/0144593 A1 | 7/2003 | Whitmore et al. |
| 2003/0212331 A1 | 11/2003 | Fenton et al. |
| 2003/0212332 A1 | 11/2003 | Fenton et al. |
| 2003/0220568 A1 | 11/2003 | Hansmann et al. |
| 2004/0006336 A1 | 1/2004 | Swanson |
| 2004/0030268 A1 | 2/2004 | Weng et al. |
| 2004/0041880 A1 | 3/2004 | Ikeda et al. |
| 2004/0127791 A1 | 7/2004 | Mast et al. |
| 2004/0143252 A1 | 7/2004 | Hurst |
| 2005/0015107 A1 | 1/2005 | O'Brien |
| 2005/0131298 A1 | 6/2005 | Cai |
| 2005/0137520 A1 | 6/2005 | Rule et al. |
| 2005/0228286 A1 | 10/2005 | Messerly et al. |
| 2005/0240125 A1 | 10/2005 | Makin et al. |
| 2005/0261585 A1 | 11/2005 | Makin et al. |
| 2005/0261587 A1 | 11/2005 | Makin et al. |
| 2005/0261588 A1 | 11/2005 | Makin et al. |
| 2005/0261610 A1 | 11/2005 | Mast et al. |
| 2005/0267488 A1 | 12/2005 | Hare et al. |
| 2006/0052701 A1 | 3/2006 | Carter et al. |
| 2006/0173348 A1 | 8/2006 | Wilser et al. |
| 2006/0235306 A1 | 10/2006 | Cotter et al. |
| 2007/0004984 A1 | 1/2007 | Crum et al. |
| 2007/0021691 A1 | 1/2007 | Nita et al. |

FOREIGN PATENT DOCUMENTS

| | | |
|---|---|---|
| JP | 10-14967 | 1/1989 |
| JP | 04-307044 | 10/1992 |
| JP | 08-084470 | 3/1996 |
| JP | 08-084740 | 4/1996 |
| JP | 9098980 | 4/1997 |
| JP | 09-192139 | 7/1997 |
| JP | 10-216146 | 8/1998 |
| JP | 10-511477 | 11/1998 |
| JP | 11-313832 | 11/1999 |
| JP | 2000-116657 | 4/2000 |
| JP | 2000-126185 | 5/2000 |
| JP | 2000-126197 | 5/2000 |
| JP | 2000-237205 | 9/2000 |
| JP | 2001-104358 | 4/2001 |
| WO | 95/29737 | 11/1995 |
| WO | 97/29709 | 8/1997 |
| WO | WO 98/58588 | 12/1998 |
| WO | 99/33500 | 7/1999 |
| WO | 00/38580 | 7/2000 |
| WO | WO 01/34018 | 5/2001 |
| WO | 01/43641 | 6/2001 |
| WO | 01/45550 A2 | 6/2001 |
| WO | 01/45550 A3 | 12/2001 |
| WO | 01/97702 | 12/2001 |
| WO | 03/075711 | 9/2003 |
| WO | 03/075771 | 9/2003 |
| WO | 2005/058138 | 6/2005 |
| WO | 2005/072084 | 8/2005 |

OTHER PUBLICATIONS

Maass-Moreno, R. et al., "Noninvasive temperature estimation in tissue via ultrasound echo-shifts. Part I Analytical model," *J. Acoust. Soc. Am.*, 100 (4), Pt. 1, pp. 2514-2521 (Oct. 1996).

Maass-Moreno, R. et al., "Noninvasive temperature estimation in tissue via ultrasound echo-shifts. Part II. In vitro study," *J. Acoust Soc. Am.*, 100 (4), Pt. 1, pp. 2522-2530 (Oct. 1996).

Seip R. et al., "Noninvasive Real-Time Multipoint Temperature Control for Ultrasound Phased Array Treatments," *IEEE Transactions on Ultrasonics, Ferroelectrics, and Frequency Control*, vol. 43, No. 6, pp. 1063-1073 (Nov. 1996).

Simon, C. et al., "Two-Dimensional Temperature Estimation Using Diagnostic Ultrasound," *IEEE Transactions of Ultrasonics, Ferroelectrics, and Frequency Control*, vol. 45, No. 4, pp. 1088-1099 (Apr. 1998).

Supplementary Partial European Search Report, European Application No. 04814036.2 (Apr. 3, 2009).

Supplementary Partial European Search Report, European Application No. 04811946.5 (Oct. 30, 2008).

AU, Examiners Report, Australian Application No. 2002303862 (Nov. 25, 2005).

AU, Examiners Report, Australian Application No. 2002305713 (Jan. 31, 2006).

AU, Examiners Report, Australian Application No. 2002310089 (Oct. 20, 2005).

AU, Examiners Report, Australian Application No. 2002312084 (Sep. 26, 2005).

AU, Examiners Report, Australian Application No. 2002314817 (Sep. 22, 2005).

CA, Office Action, Canadian Application No. 2,448,906 (Jan. 31, 2008).

CA, Office Action, Canadian Application No. 2,449,062 (Jan. 31, 2008).

CA, Office Action, Canadian Application No. 2,449,568 (Jan. 31, 2008).

Cain, C.A. et al., "Concentric-Ring and Sector-Vortex Phased-Array Applicators for Ultrasound Hyperthermia," *IEEE Transactions on Microwave Theory and Techniques*, vol. MTT-34, No. 5, pp. 542-551 (May 1986).

Chavrier, F. et al., "Modeling of high-intensity focused ultrasound-induced lesions in the presence of cavitation bubbles," *J. Acoust. Soc. Am.*, 108 (1), pp. 432-440 (Jul. 2000).

Christensen, D.A., *Ultrasonic Bioinstrumentation*, 1988, John Wiley and Sons, p. 105, p. 155.

Clare, M.C. et al., "MRI Guided Focused Ultrasound Surgery (FUS) of uterine leiomyomas: A Feasibility Study," workshop of MRI Guided: Focused Ultrasound Surgery, 2002, Syllabus, International Society for Magnetic Resonance in Medicine.

Cool-tip™ RF Radio Frequency Ablation System, web page from radionics.com.

Daum, D.R. et al., "Thermal Dose Optimization Via Temporal Switching in Ultrasound Surgery," *IEEE Transactions on Ultrasonics, Ferroelectrics, and Frequency Control*, vol. 45, No. 1, pp. 208-215 (Jan. 1998).

Electrosurgical Devices, RF Generator and RITA Base Software, web page of Rita Medical Systems, www.ritamedical.com.

EP, Supplementary Partial European Search Report, European Application No. 04811946.5 (Oct. 30, 2008).

Hill, C.R. et al., "Lesion Development in Focused Ultrasound Surgery: A General," *Ultrasound in Med. & Biol.*, 1994, pp. 259-269, vol. 20, No. 3, Elsevier Science ltd., New York, USA.

McGough, R.J. et al., "Mode scanning: heating pattern synthesis with ultrasound phased arrays," *Int. J. Hyperthermia*, 1994, vol. 10, No. 3, pp. 433-442.

PCT, International Preliminary Examination Report, International Application No. PCT/US02/16695 (Nov. 13, 2002).

PCT, International Preliminary Examination Report, International Application No. PCT/US02/16512 (Sep. 8, 2003).
PCT, International Preliminary Examination Report, International Application No. PCT/US02/16699 (Aug. 25, 2003).
PCT, International Preliminary Examination Report, International Application No. PCT/US02/16700 (May 30, 2004).
PCT, International Preliminary Examination Report, International Application No. PCT/US02/16696 (May 5, 2003).
PCT, International Preliminary Examination Report, International Application No. PCT/US02/16421 (May 19, 2003).
PCT, International Preliminary Examination Report, International Application No. PCT/US02/16697 (Apr. 23, 2003).
PCT, International Preliminary Examination Report, International Application No. PCT/US02/16417 (May 2, 2003).
PCT, International Preliminary Examination Report, International Application No. PCT/US02/16689 (Feb. 19, 2003).
PCT, International Search Report, International Application No. PCT/US02/16695 (dated Sep. 24, 2002; published Dec. 5, 2002).
PCT, International Search Report, International Application No. PCT/US02/16512 (dated Jul. 17, 2003; published Sep. 25, 2003).
PCT, International Search Report, International Application No. PCT/US02/16699 (dated Jul. 17, 2003; published Nov. 20, 2003).
PCT, International Search Report, International Application No. PCT/US02/16700 (dated Apr. 15, 2003; published 70/24/2003).
PCT, International Search Report, International Application No. PCT/US02/16696 (dated Apr. 4, 2003; published Nov. 6, 2003).
PCT, International Search Report, International Application No. PCT/US02/16421 (dated Apr. 4, 2003; published Mar. 18, 2004).
PCT, International Search Report, International Application No. PCT/US02/16697 (dated Mar. 31, 2003; published Nov. 6, 2003).
PCT, International Search Report, International Application No. PCT/US02/16417 (dated Mar. 26, 2003; published Mar. 11, 2004).
PCT, International Search Report, International Application No. PCT/US02/16689 (dated Dec. 18, 2002; published Apr. 17, 2003).
Seip, R. et al., "Comparison of Transducer Geometries and Excitation Configurations for Transrectal Prostate HIFU Treatments," *2001 IEEE Ultrasonics Symposium*, pp. 1343-1346.
Vaezy, S. et al., Treatment of Uterine Fibroid Tumors in a Nude Mouse Model Using High-Intensity Focused Ultrasound, *Am. J. Obstet. Gynecol.*, 2000, pp. 6-11, vol. 183, No. 1.
U.S. Appl. No. 10/152,766 and the prosecution history thereof.
U.S. Appl. No. 10/152,769 and the prosecution history thereof.
U.S. Appl. No. 10/153,122 and the prosecution history thereof.
U.S. Appl. No. 10/153,241 and the prosecution history thereof.
U.S. Appl. No. 10/153,245 and the prosecution history thereof.
U.S. Appl. No. 10/153,510 and the prosecution history thereof.
U.S. Appl. No. 10/867,170 and the prosecution history thereof.
U.S. Appl. No. 10/735,045 and the prosecution history thereof.
U.S. Appl. No. 10/795,680 and the prosecution history thereof.
U.S. Appl. No. 10/850,984 and the prosecution history thereof.
U.S. Appl. No. 12/145,635 and the prosecution history thereof.

* cited by examiner

METHOD FOR MONITORING OF MEDICAL TREATMENT USING PULSE-ECHO ULTRASOUND

This is a continuation-in-part of application Ser. No. 10/153,241, filed May 22, 2002, now abandoned which claims priority to provisional application Ser. No. 60/294,135 filed May 29, 2001. The present invention relates generally to ultrasound, and more particularly, to an ultrasound medical imaging method.

FIELD OF THE INVENTION

Background of the Invention

Ultrasound medical systems and methods include ultrasound imaging of anatomical tissue to identify tissue for medical treatment. Ultrasound may also be used to medically treat and destroy unwanted tissue by heating the tissue. Imaging is done using low-intensity ultrasound waves, while medical treatment is performed with high-intensity ultrasound waves. High-intensity ultrasound waves, when focused at a focal zone a distance away from the ultrasound source, will substantially medically affect tissue in the focal zone. However, the high-intensity ultrasound will not substantially affect patient tissue outside the focal zone, such as tissue located between the ultrasound source and the focal zone. Other treatment regimes of interest include unfocused high-intensity ultrasound, wherein the ultrasound energy is distributed over a relatively broad region of tissue rather than being generally concentrated within a focal zone.

Ultrasound waves may be emitted and received by a transducer assembly. The transducer assembly may include a single element, or an array of elements acting together, to image the anatomical tissue and to ultrasonically ablate identified tissue. Transducer elements may employ a concave shape or an acoustic lens to focus ultrasound energy. Transducer arrays may include planar, concave or convex elements to focus or otherwise direct ultrasound energy. Further, such array elements may be electronically or mechanically controlled to steer and focus the ultrasound waves emitted by the array to a focal zone to provide three-dimensional medical ultrasound treatment of anatomical tissue. In some treatments the transducer is placed on the surface of the tissue for imaging and/or treatment of areas within the tissue. In other treatments the transducer is surrounded with a balloon which is expanded to contact the surface of the tissue by filling the balloon with a fluid such as a saline solution to provide acoustic coupling between the transducer and the tissue.

Examples of ultrasound medical systems and methods include: deploying an end effector having an ultrasound transducer outside the body to break up kidney stones inside the body; endoscopically inserting an end effector having an ultrasound transducer into the rectum to medically destroy prostate cancer; laparoscopically inserting an end effector having an ultrasound transducer into the abdominal cavity to destroy a cancerous liver tumor; intravenously inserting a catheter end effector having an ultrasound transducer into a vein in the arm and moving the catheter to the heart to medically destroy diseased heart tissue; and interstitially inserting a needle end effector having an ultrasound transducer into the tongue to medically destroy tissue to reduce tongue volume as a treatment for snoring. Methods for guiding an end effector to the target tissue include x-rays, Magnetic Resonance Images ("MRI") and images produced using the ultrasound transducer itself.

Low-intensity ultrasound energy may be applied to unexposed anatomical tissue for the purpose of examining the tissue. Ultrasound pulses are emitted, and returning echoes are measured to determine the characteristics of the unexposed tissue. Variations in tissue structure and tissue boundaries have varying acoustic impedances, resulting in variations in the strength of ultrasound echoes. A common ultrasound imaging technique is known in the art as "B-Mode" wherein either a single ultrasound transducer is articulated or an array of ultrasound transducers is moved or electronically scanned to generate a two-dimensional image of an area of tissue. The generated image is comprised of a plurality of pixels, each pixel corresponding to a portion of the tissue area being examined. The varying strength of the echoes is preferably translated to a proportional pixel brightness. A cathode ray tube or liquid crystal display can be used to display a two-dimensional pixellated image of the tissue area being examined varying strength of the echoes is preferably translated to a proportional pixel brightness. A cathode ray tube or liquid crystal display can be used to display a two-dimensional pixellated image of the tissue area being examined.

When high-intensity ultrasound energy is applied to anatomical tissue, significant beneficial physiological effects may be produced in the tissue. For example, undesired anatomical tissue may be ablated by heating the tissue with high-intensity ultrasound energy. By focusing the ultrasound energy at one or more specific focusing zones within the tissue, thermal effects can be confined to a defined region that may be remote from the ultrasound transducer. The use of high-intensity focused ultrasound to ablate tissue presents many advantages, including: reduced patient trauma and pain; potentially reduced patient recovery time; elimination of the need for some surgical incisions and stitches; reduced or obviated need for general anesthesia; reduced exposure of non-targeted internal tissue; reduced risk of infection and other complications; avoidance of damage to non-targeted tissue; avoidance of harmful cumulative effects from the ultrasound energy on the surrounding non-target tissue; reduced treatment costs; minimal blood loss; and the ability for ultrasound treatments to be performed at non-hospital sites and/or on an out-patient basis.

Ultrasound treatment of anatomical tissue may involve the alternating use of both low-intensity imaging ultrasound and high-intensity treatment ultrasound. During such treatment, imaging is first performed to identify and locate the tissue to be treated. The identified tissue is then medically treated with high-intensity ultrasound energy for the purpose of ablating the tissue. After a period of exposure to high-intensity ultrasound, a subsequent image of the tissue is generated using low-intensity ultrasound energy to determine the results of the ultrasound treatment and provide visual guidance to the user to aid in subsequent treatments. This process of applying low-energy ultrasound to assist in guiding the position and focal point of the transducer, followed by high-energy ultrasound to ablate the undesired anatomical tissue, may continue until the undesired tissue has been completely ablated.

Although this conventional B-Mode ultrasound imaging provides an effective means for imaging tissue that is in a static state, imaging of the tissue becomes more problematic when used in conjunction with thermal high-intensity ultrasound treatment. As the tissue is ablated during treatment, the heating effects of ultrasound upon the tissue often result in qualitative changes in echo strength, causing brightness variations in the pixel display that do not consistently correspond spatially to the tissue being treated. These brightness variations result in an image display that does not represent the actual shape and size of the region of tissue that is being thermally modified by the treatment, introducing some visual ambiguity to the image.

Several methods are known for monitoring thermal ablation using B-Mode ultrasound imaging. Most of these are based on changes in the energy of ultrasound echoes, and include simple B-Mode displays of echo amplitude, estimates of tissue attenuation from analysis of distal shadowing, and quantification of changes in echo energy. Each of these methods have significant shortcomings because the tissue being treated can appear hyperechoic for reasons other than thermal ablation and because image changes must be qualitatively perceived by the user.

The most successful known methods for monitoring thermal ablation using ultrasound are based on analysis of changes in echo energy rather than a direct analysis of the echo energy. Automatic and quantitative displays of changes in echo energy or tissue attenuation are possible and can help users isolate thermally-induced changes from pre-existing echo characteristics. However, since such methods require integration of echoes over substantial regions of an image scan or "frame," the resulting images are very limited in spatial resolution. Although energy increases (and therefore B-Mode brightness increases) correspond roughly to lesion (i.e., the thermally treated tissue) position, typically the shape and size of the mapped energy increases do not always spatially correspond to actual lesions, and sometimes are either absent or otherwise unapparent.

There is a need for an improved method of ultrasound imaging that can be utilized in conjunction with therapeutic ultrasound treatment that monitors the thermal effects of the treatment on targeted tissue with greater accuracy and resolution.

SUMMARY OF THE INVENTION

The present invention overcomes the limitations of the known art by mapping differences between a first and second echo signal, each signal being obtained at different instants of time. The first and second signals are typically separated by a small time interval. The first and second signals are processed, then a measure of the amplitude of the differences between the first and second signals is made (as contrasted with a measure of the differences in signal amplitude). This difference signal is then spatially filtered and scaled to quantify echo changes associated with changes in tissue state. Difference signals may be summed over multiple time periods to obtain a cumulative map of the changes in the tissue. The resulting signals may be used to generate an ultrasound image that is more representative of the tissue as treatment progresses, providing additional information about where thermal effects are occurring. This allows for verification of successful treatment and modification of unsuccessful treatment. Known ultrasound imaging and treatment transducers may be used, providing users with increased accuracy without a need for special end effectors.

BRIEF DESCRIPTION OF THE DRAWINGS

Further features of the present invention will become apparent to those skilled in the art to which the present invention relates from reading the following specification with reference to the accompanying drawings, in which.

DETAILED DESCRIPTION

Figure 1:
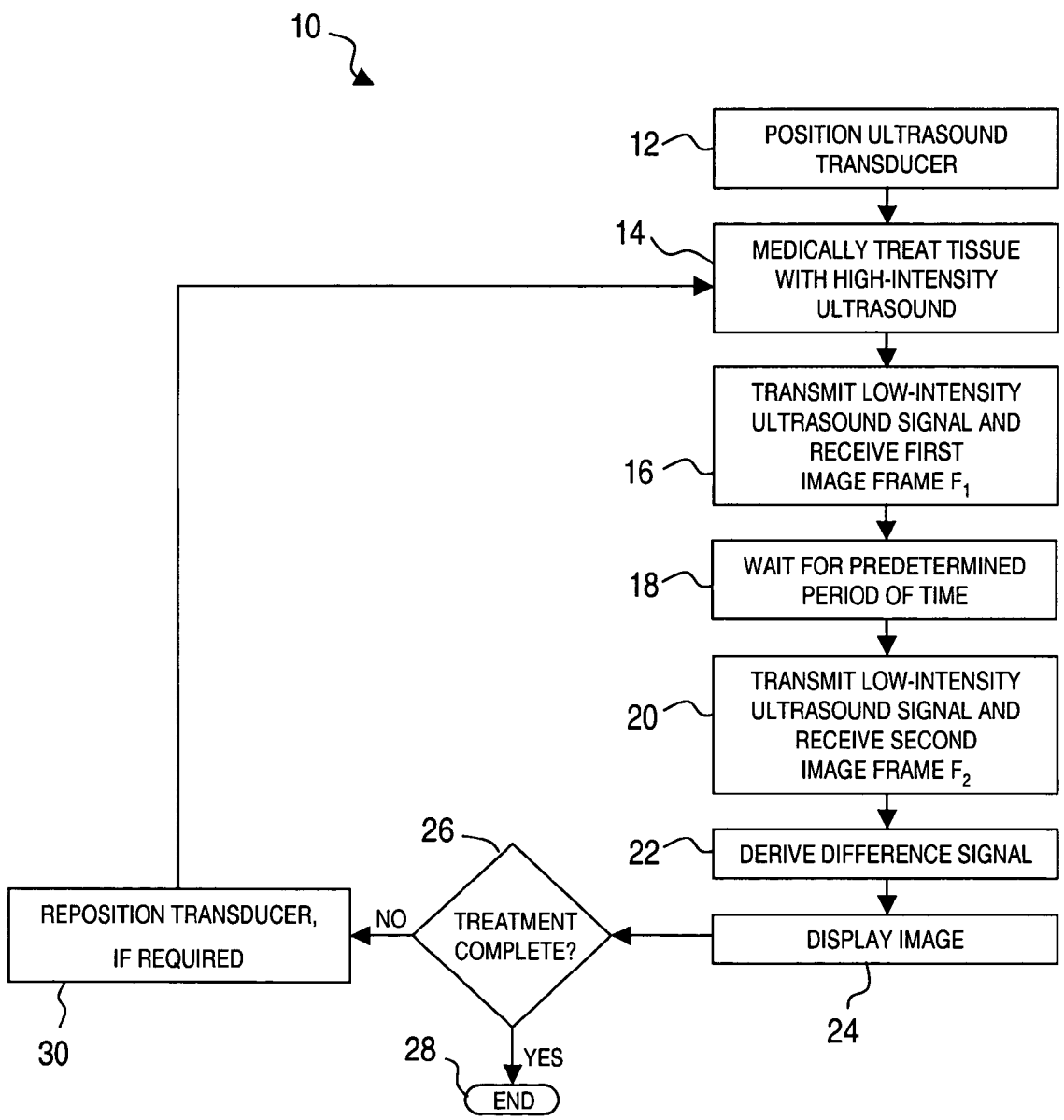
FIG. 1 is a flow diagram providing an overview of an ultrasound treatment method according to an embodiment of the present invention.

An overview of an ultrasound treatment method 10 according to an embodiment of the present invention is shown in FIG. 1. The method begins at step 12 by positioning proximate the targeted anatomical tissue to be medically treated a transducer capable of transmitting and receiving ultrasound signals. Once the transducer is in position, treatment begins at step 14 by emitting a high-intensity ultrasound signal from the transducer. The high-intensity ultrasound signal medically treats the targeted tissue, such as (but not limited to) heating the tissue to ablate the material. At step 16 a low-intensity ultrasound signal, such as a B-Mode signal, is emitted from the transducer and the reflected signals are received to form a first image frame $F_1$. It is understood that the terminology "image" includes, without limitation, creating an image in a visual form and displayed, for example, on a monitor, screen or display, and creating an image in electronic form which, for example, can be used by a computer without first being displayed in visual form. After the first image frame $F_1$ is received at step 16, a predetermined waiting period is executed at step 18 before proceeding further. It is to be understood that the predetermined waiting period may vary in value from zero seconds upwardly to a maximum of several seconds, but preferably is in the range of milliseconds. After the predetermined wait period has been completed, a low intensity ultrasound signal is again emitted from the transducer and a second image frame $F_2$ is received at step 20. At step 22 a difference signal is derived from the image frames $F_1$ and $F_2$, as will be discussed in greater detail below. The difference signal of step 22 is displayed as an image at step 24 to obtain a visual indication of the tissue change as a result of the medical treatment of step 14. It should be noted that the visual indication of the tissue change provided by the present invention differs from the post-treatment image of the prior art in that the present invention provides an image showing echo differences in contrast to echos from the target tissue. The image of echo differences can indicate whether treatment is complete. If treatment is complete at step 26 (for example, the targeted tissue has been fully ablated), the method is ended at step 28. However, if the tissue requires additional treatment, the transducer may be re-positioned at step 30. The method then returns to step 14 to continue medical treatment of the targeted tissue.

Figure 2:
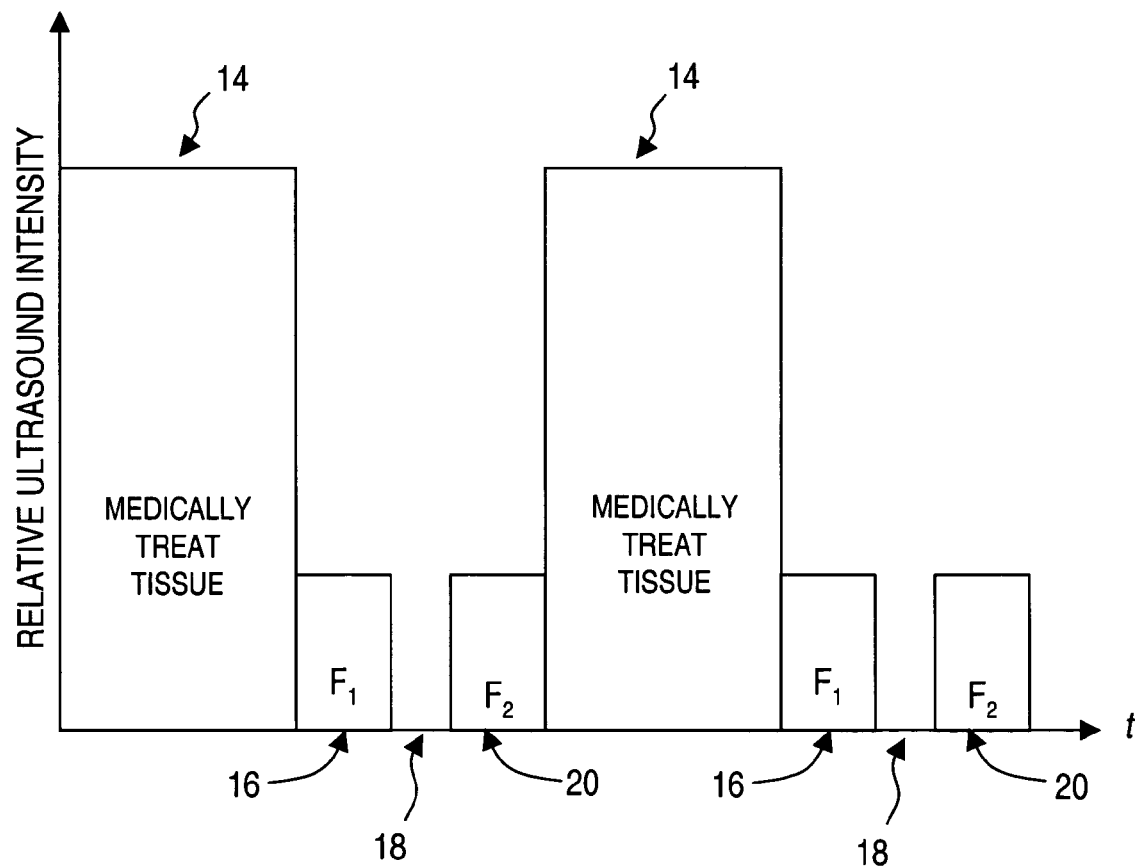
FIG. 2 illustrates the relative amplitude and timing of ultrasound image frames and ultrasound treatments of the method of FIG. 1.

Referring additionally to FIG. 2, the method of FIG. 1 is illustrated in relation to a time scale t. The targeted tissue is medically treated with a relatively high-intensity ultrasound signal as at step 14. Then, at step 16 a relatively low-intensity B-Mode image scan frame $F_1$ is received. After a predetermined off-time, as at step 18, a second image frame F2 is received, as at step 20. The image frames $F_1$ and $F_2$ each contain a signal representing the same portion of the target tissue. For each image frame, a number of A-lines of raw echo signal data are received, the number of each line corresponding to azimuthal position and the signal time corresponding to depth.

Figure 3:
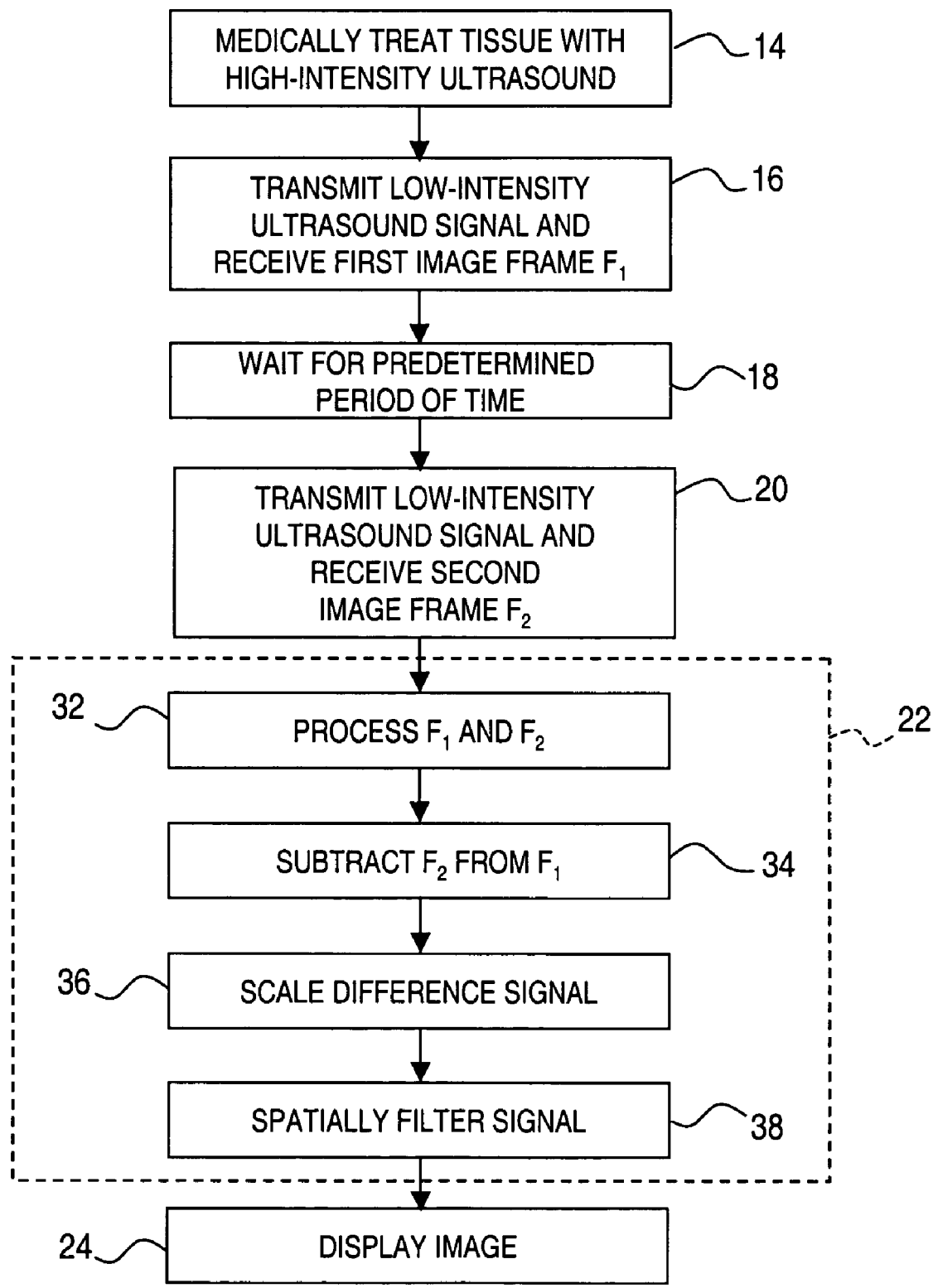
FIG. 3 is a flow diagram of a method for monitoring medical treatment of anatomical tissue using pulse-echo ultrasound according to an embodiment of the present invention.
Figure 4:
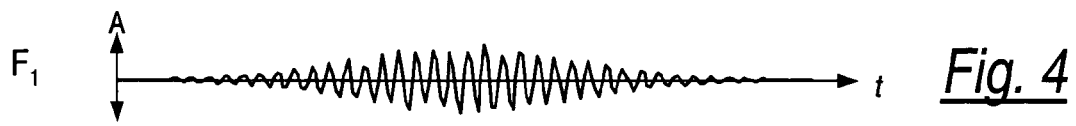
FIG. 4 is a view of a first ultrasound signal on a time scale.
Figure 5:
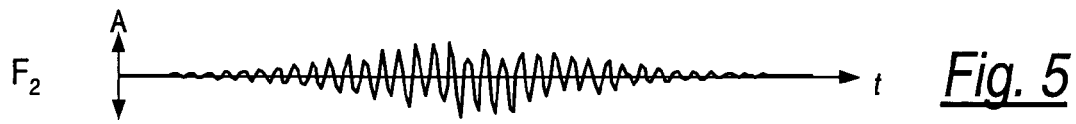
FIG. 5 is a view of a second ultrasound signal on a time scale.
Figure 6:
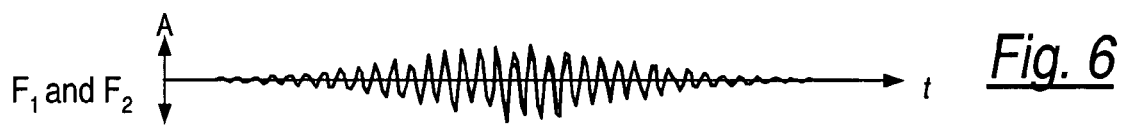
FIG. 6 is a composite view of the signals of FIG. 4 and FIG. 5.
Figure 7:
FIG. 7 is a view showing the difference signal computed from FIG. 4 and FIG. 5.
Figure 8:
FIG. 8 is a view showing the absolute value of the difference signal of FIG. 7.
Figure 9:
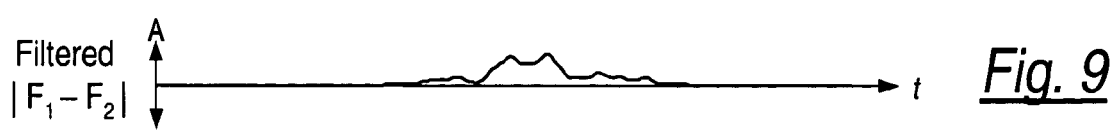
FIG. 9 is a view of the signal of FIG. 8 after filtering.

Referring now to FIG. 3 in combination with FIGS. 1 and 2, a method for monitoring medical treatment of anatomical tissue including, but not limited to, thermal ablation according to an embodiment of the present invention is depicted. An ultrasound transducer is positioned proximate the targeted anatomical tissue. The tissue may then be medically treated such as by ablation using high-intensity ultrasound waves for a period of time as at step 14. At step 16 a first image frame $F_1$ (such as is illustrated in FIG. 4) is received. The image frame may optionally be stored electronically, such as in a computer, magnetic media and solid-state memory. A second image frame $F_2$, separated from $F_1$ by a fixed time interval of step 18, is received at step 20. An example image frame $F_2$ is illustrated in FIG. 5. A difference signal is then derived at step 22 by means of steps 32-38. The raw echo signals of frames $F_1$ and $F_2$ may be processed at step 32, such as to obtain complex analytic signals by means of a Hilbert transformation. A difference signal may then be derived by subtracting the signal of image frame $F_2$ from the signal of $F_1$ at step 34. The difference signal of step 34 may take into account both phase and amplitude differences between $F_1$ and $F_2$, computing the amplitude of the signal differences (as opposed to differences in signal amplitude) of $F_1$ and $F_2$. A composite illustration of image frames $F_1$ and $F_2$ is shown in FIG. 6, while the derived difference signal is depicted in FIG. 7. At step 36 the difference signal may be scaled to a convenient value, such as the mean squared value of the difference signal, the mean squared value of one of the original echo signals, or a mathematical constant. As an example, a signal representing the scaled absolute value of the difference signal of FIG. 7 is shown in FIG. 8. Other functions of the difference signal, such as its squared absolute value or logarithm, may similarly be employed. Still other scaling algorithms may use the amplitude and/or phase of the first and second signals to enhance differences between the first and second signals. Details of such algorithms are left to the skilled artisan. At step 38 the difference signal is spatially filtered, as depicted in FIG. 9, to smooth small-scale random variations. Spatial filtering of the scaled difference signal is represented by Equation 1.

$$\Psi(x, z) = \int_{-\infty}^{\infty} \int_{-\infty}^{\infty} w(x - x, z - z_0) |p_0(x_0, z_0) - p_1(x_0, z_0)|^2 \, dx_0 \, dz_0$$

Equation 1

In Equation 1 $\Psi$ is a spatial difference map (image) of the scaled and filtered difference signal. The filtering may be performed by convolution of the scaled difference signal with a two-dimensional window w. This convolution may be efficiently performed through the use of two-dimensional Fast Fourier Transform ("FFT") operations.

The difference signal may be normalized to have a maximum value of 1. This approach would result in a spatial map of the echo decorrelation, similar to measures of turbulence in color Doppler imaging systems. However, instead of examining echo decorrelation (a normalized measure of echo differences), a non-normalized map is considered preferable for the present invention because the echo difference is then enhanced in regions of greater echogenicity. Since hyperechoicity is one correlate to tissue ablation, this feature increases the specificity of the method for monitoring thermal ablative medical treatment by providing an image with greater detail.

The spatially filtered signal of FIG. 9 is then displayed as an image at step 24 (see FIG. 3), in any manner previously discussed.

Figure 10:
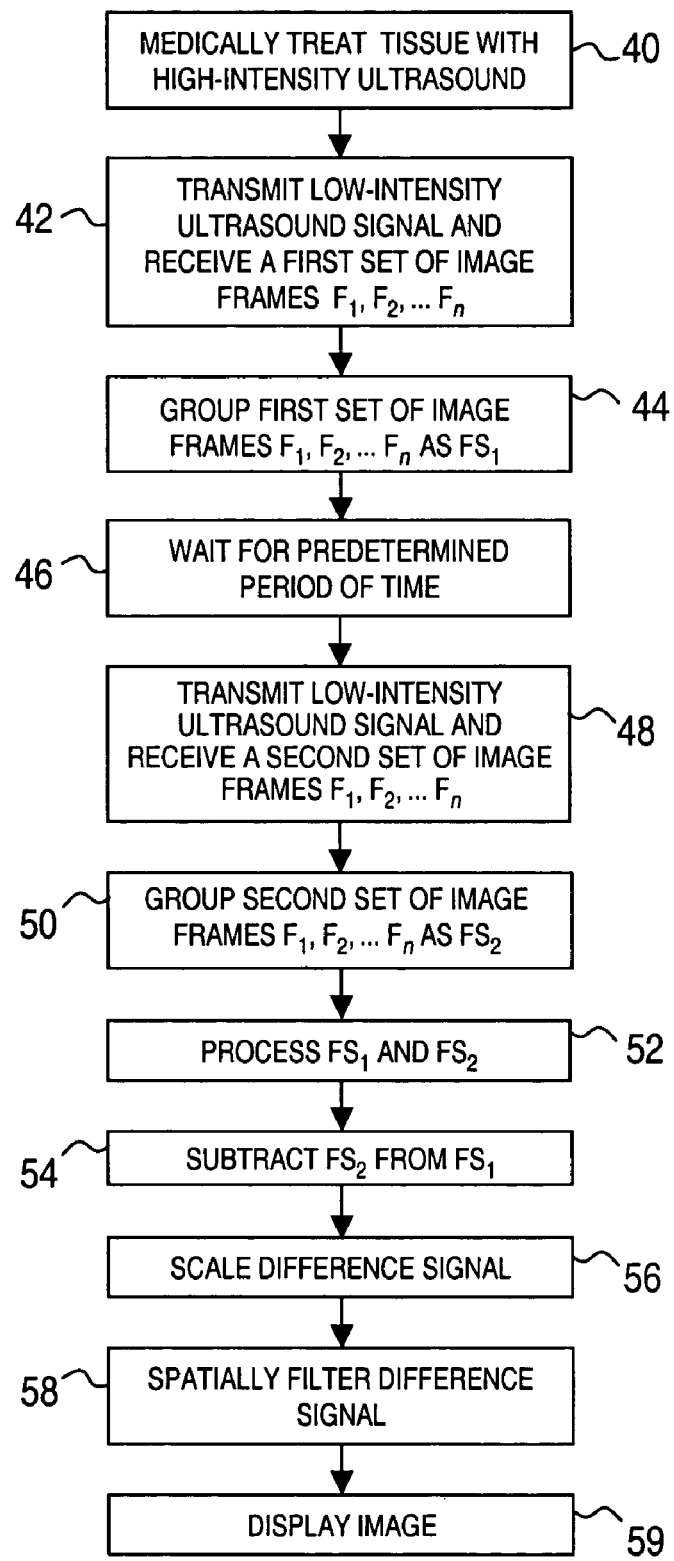
FIG. 10 is a flow diagram depicting a method for monitoring medical treatment of anatomical tissue using pulse-echo ultrasound according to an alternate embodiment of the present invention.
Figure 11:
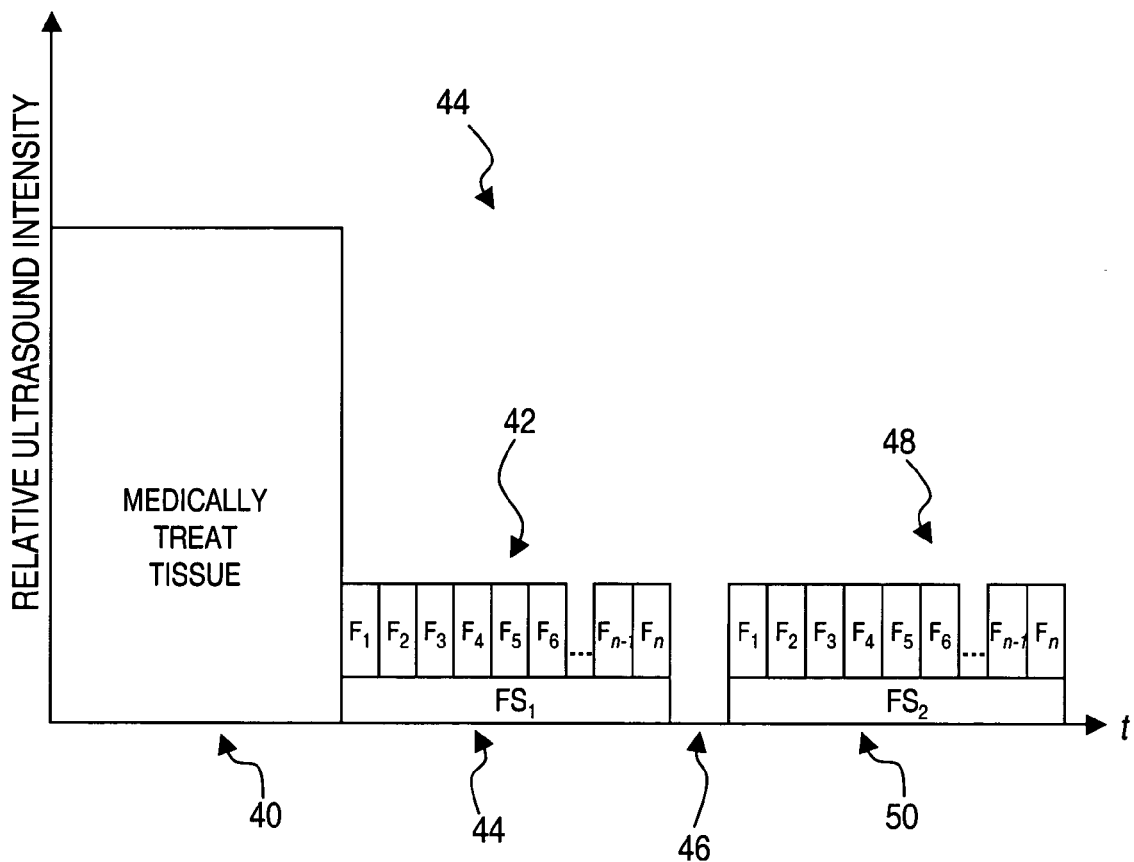
FIG. 11 illustrates the relative amplitude and timing of ultrasound image frames, image frame sets and ultrasound treatments of the method of FIG. 10.

In a second embodiment of the present invention, ultrasound images may be generated as depicted in FIGS. 10 and 11. At step 40 the tissue is medically treated with high-intensity ultrasound waves. At step 42 a succession of image frames, depicted as $F_1, F_2, \ldots F_n$, are received. The image frames $F_1, F_2, \ldots F_n$ each contain a signal representing the same portion of the target tissue. At step 44 the image frames $F_1, F_2, \ldots F_n$ are mathematically grouped, such as by summing or averaging, to form a first image frame set labeled $FS_1$, as shown in FIG. 11. After waiting a predetermined amount of time, as at step 46, a second set of image frames $F_1, F_2, \ldots F_n$ are received at step 48. At step 50 the second set of image frames $F_1, F_2, \ldots F_n$ are mathematically grouped, such as by summing or averaging, to form a second image frame set $FS_2$ as shown in FIG. 11. The raw echo signals of image frame sets $FS_1$ and $FS_2$ may be processed at step 52, such as to derive complex analytic signals by means of a Hilbert transformation. The signal of image frame set $FS_2$ is then subtracted from the signal of image frame set $FS_1$ at step 54 to derive a difference signal. The difference signal may take into account both phase and amplitude differences between $FS_1$ and $FS_2$, computing the amplitude of the signal differences (as opposed to differences in signal amplitude) of $FS_1$ and $FS_2$. At step 56 the difference signal may be scaled to a convenient value using any scaling methods and algorithms, previously described or otherwise. At step 58 the difference signal is spatially filtered to smooth small-scale random variations before being displayed as an image at step 59. This embodiment of the present invention may provide a more robust map of the backscatter changes by reducing the influence of random signal variations caused by rapid transient effects such as violent bubble activity produced during tissue ablation.

Figure 12:
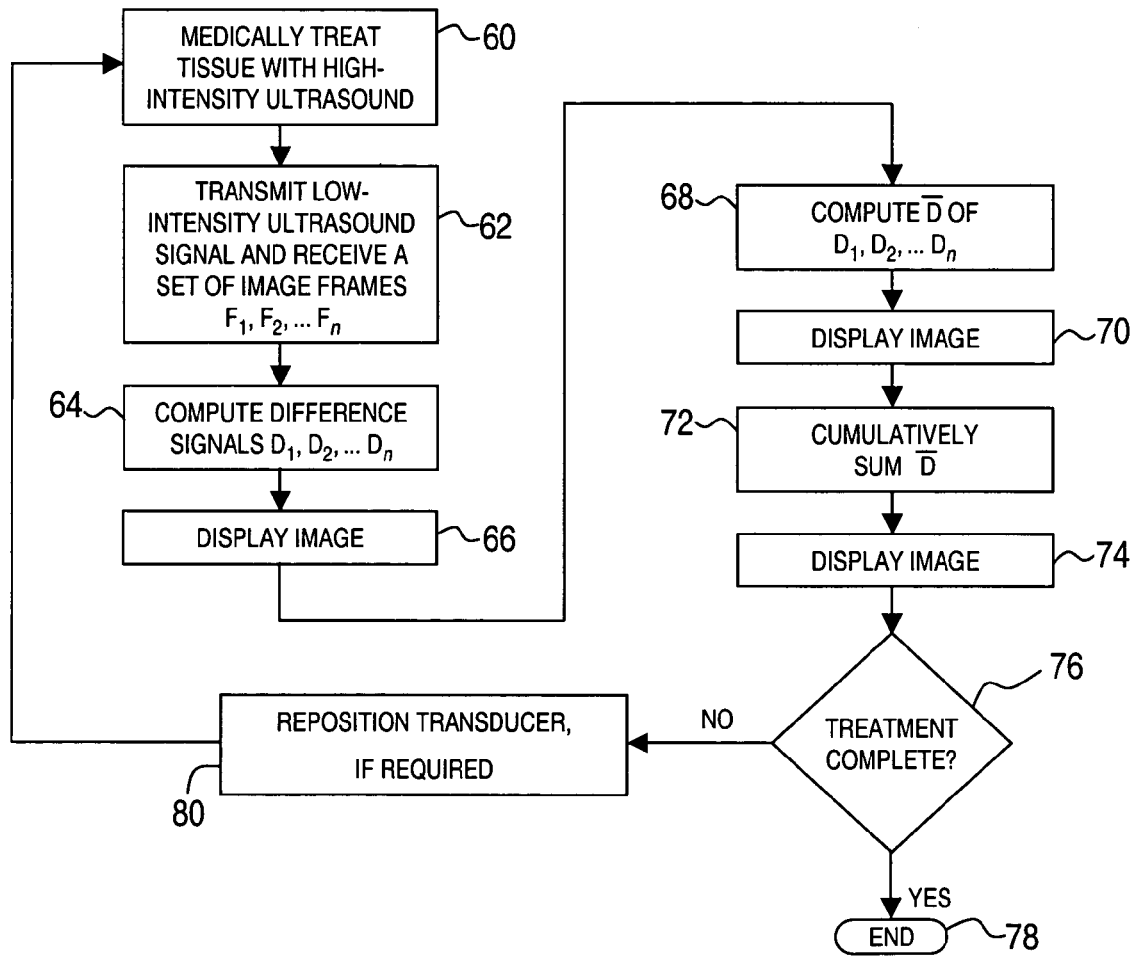
FIG. 12 depicts a flow diagram of a method for monitoring medical treatment of anatomical tissue using pulse-echo ultrasound according to another alternate embodiment of the present invention.
Figure 13:
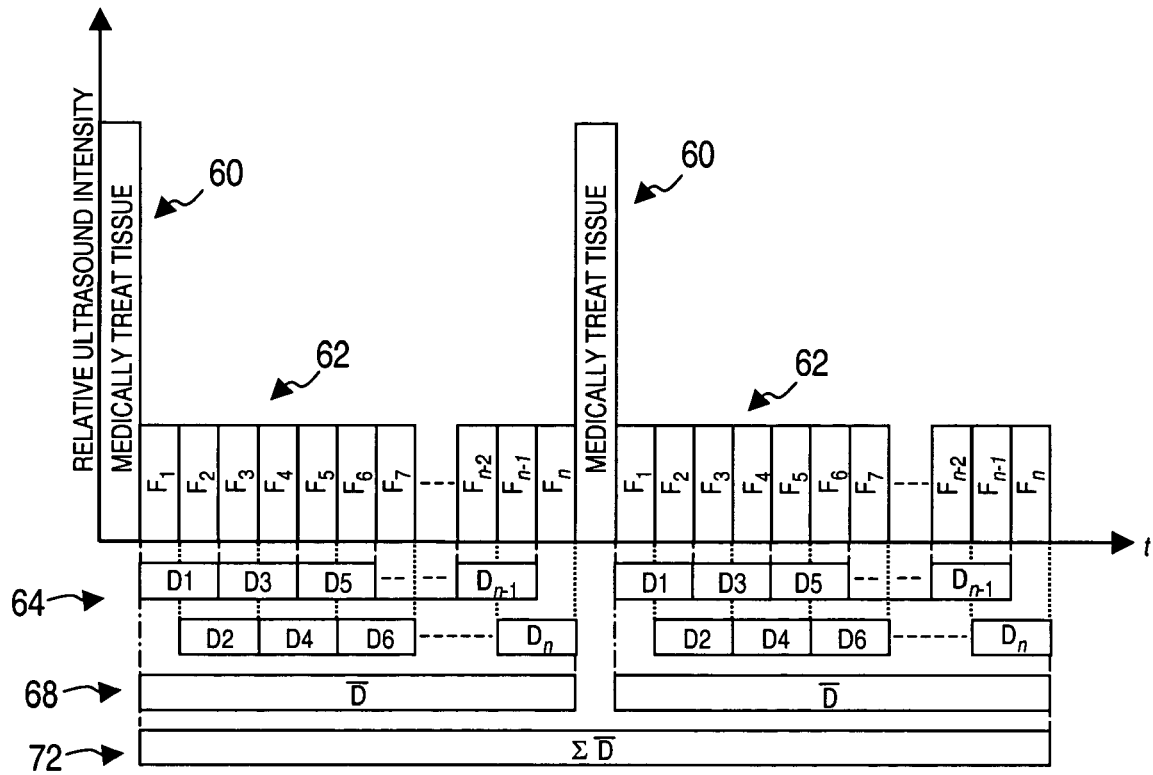
FIG. 13 shows the relative amplitude and timing of ultrasound image frame sets, difference signals and ultrasound treatments of the method of FIG. 12.

In a third embodiment of the present invention, smoothing of the image signal may alternatively be accomplished by using a plurality of image frames, as illustrated in FIGS. 12 and 13. The tissue is medically treated at step 60, then a set of image frames $F_1, F_2, \ldots F_n$ are received at step 62. A plurality of difference signals $D_1, D_2, \ldots D_n$ are computed at step 64. It should be noted that the difference signals may be computed using various arrangements of pairs of image frames. For example, difference signal $D_1$ may be formed by subtracting $F_2$ from $F_1$; likewise, $D_2$ may be formed by subtracting $F_3$ from $F_2$, as shown in FIG. 13. Other arrangements of image frame pairs may also be used, including (but not limited to) odd-numbered image frames (i.e., subtracting $F_3$ from $F_1$, etc.) and even-numbered image frames (i.e., subtracting $F_4$ from $F_2$, etc.). The pairings may be interlaced (i.e., subtracting $F_2$ from $F_1$, subtracting $F_3$ from $F_2$, etc.) or sequential (i.e., subtracting $F_2$ from $F_1$, $F_4$ from $F_3$, etc.). An indication or image may be displayed at step 66, showing at least one of the difference signals $D_1, D_2, \ldots D_n$. At step 68 the difference signals $D_1, D_2, \ldots D_n$ may be further processed, such as by averaging, to reduce artifactual content. The averaged signal, denoted as $\overline{D}$, may also be displayed as an image, as at step 70. The averaged signals may themselves be cumulatively summed, as at step 72, to provide a view of the results of successive medical treatments 60. The summed averages may be displayed at step 74. If treatment is determined to be complete at step 76, the method is ended at step 78. However, if the tissue appears to require additional treatment, the transducer may be re-positioned at step 80. The method is then repeated beginning at step 60 to continue treatment of the targeted tissue.

Figure 14:
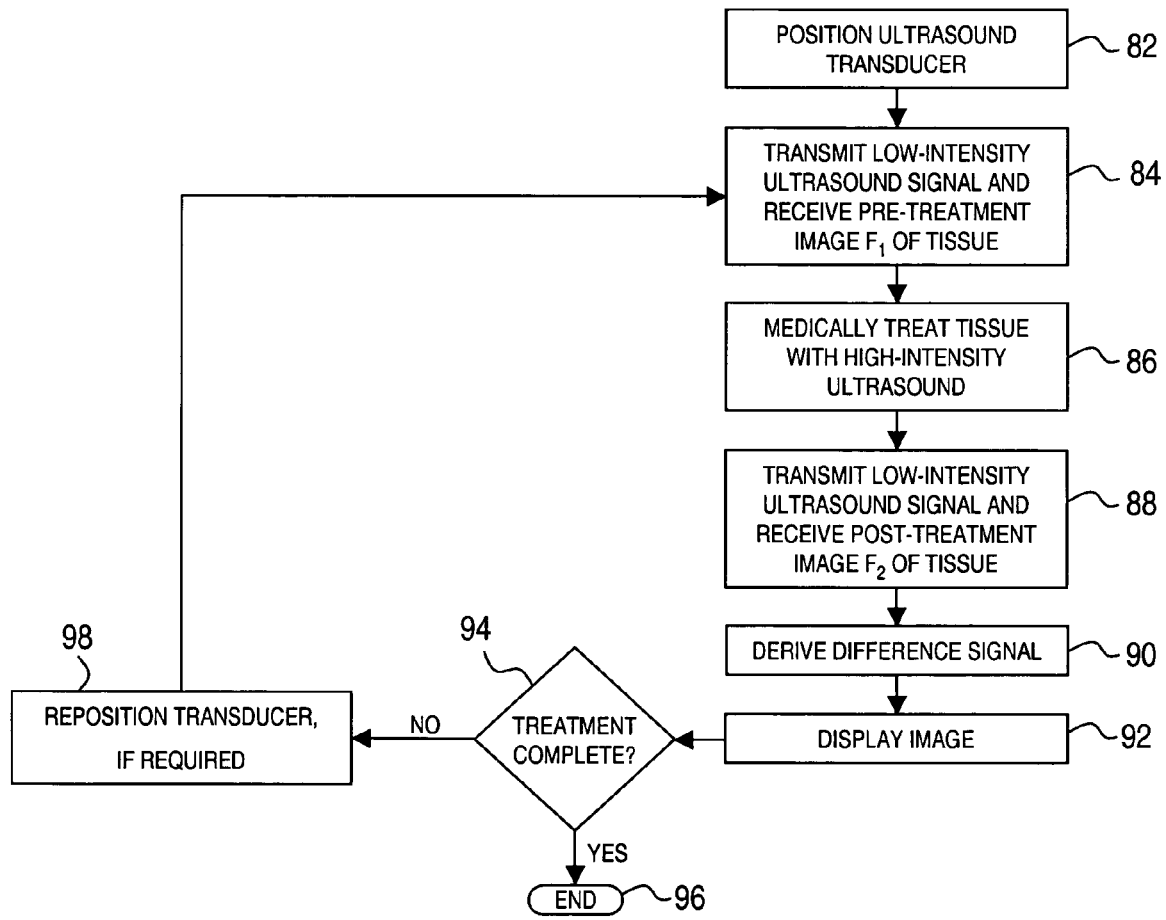
FIG. 14 is a flow diagram of a method for monitoring medical treatment of anatomical tissue using pulse-echo ultrasound according to yet another alternate embodiment of the present invention.
Figure 15:
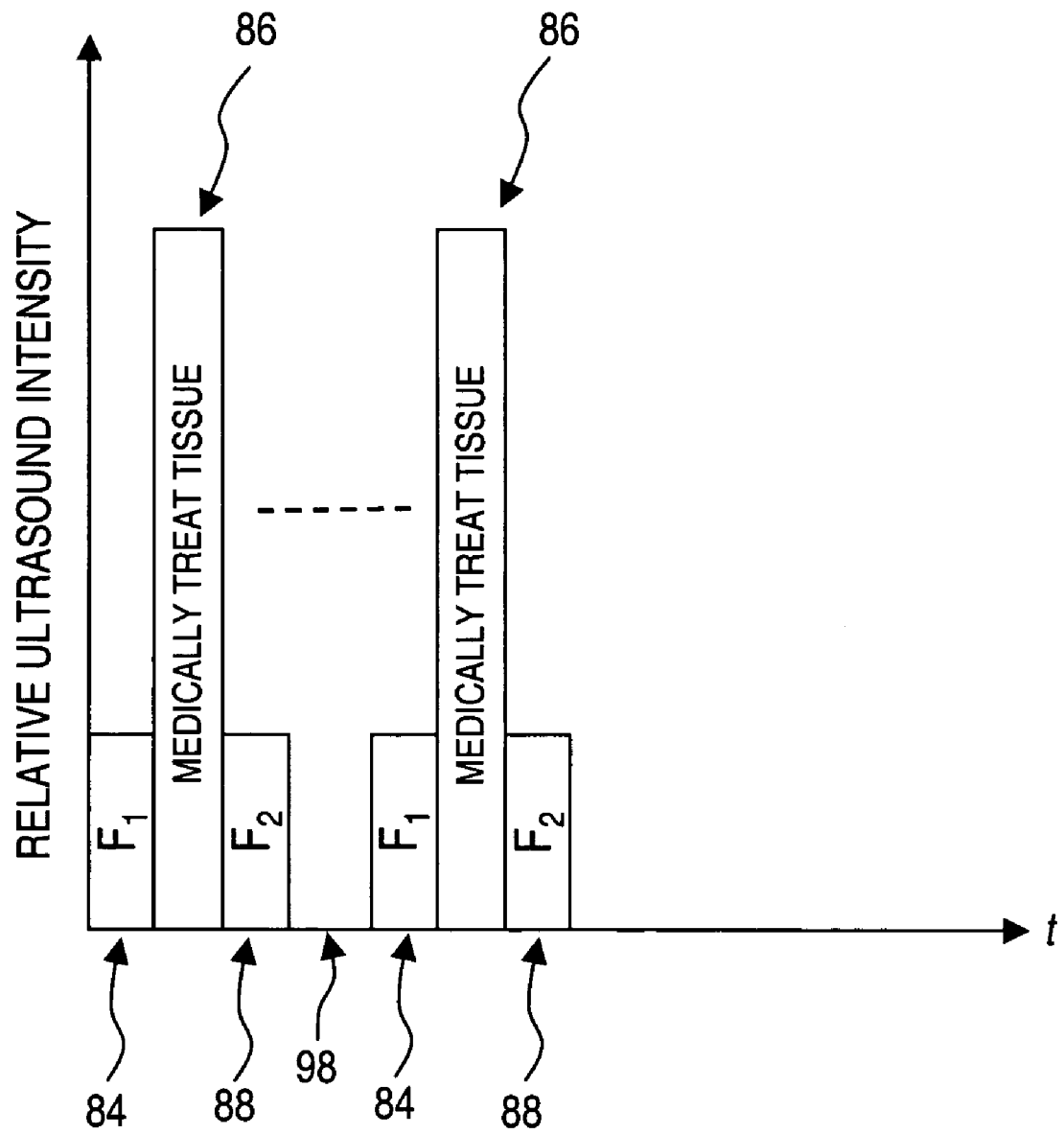
FIG. 15 shows the relative amplitude and timing of ultrasound image frames and ultrasound treatments of the method of FIG. 14.

A fourth embodiment of the present invention is shown in FIGS. 14 and 15 wherein a difference signal is derived using imaging frames generated both before and after medical treatment. At step 82 the ultrasound transducer is positioned proximate the targeted tissue to be medically treated. At step 84 a pre-treatment image frame $F_1$ is generated from received ultrasound signals. Then, at step 86 the tissue is subject to a quantum of medical treatment, such as by ablating the tissue. After a quantum of medical treatment is administered, a second image frame $F_2$ is generated at step 88. A difference signal is derived at step 90, using the data contained in image frames $F_1$ and $F_2$ in the same manner as previously described. An indication or image of the difference signal may be displayed at step 92. If treatment is determined to be complete at step 94, the method is ended at step 96. However, if the targeted tissue is determined to require additional treatment, the transducer may be re-positioned as necessary at step 98. The method is then repeated and a subsequent quantum of treatment is administered beginning at step 84.

An expected difficulty for the present invention is artifactual backscatter change due to tissue motion artifacts. This difficulty can be largely overcome by several features of the method. First, backscatter differences can be computed between image frames closely spaced in time. If the tissue moves only a small amount during the interval, motion artifacts are then small. Second, artifacts due to axial tissue motion can be removed effectively by phase compensation during signal processing. That is, before computation of the signal difference, one of the complex image frames is multiplied by a phase compensation function $e^{-i\theta}$, where $\theta$ is the low-pass filtered phase of the conjugate product of the two complex image frames. The resulting signal difference is then computed, for example, using Equation 2:

$$\Psi = \int_{-\infty}^{\infty}\int_{-\infty}^{\infty} w(x,z)|p_0(x,z) - p_1(x,z)e^{-i\varpi_0\delta t}|^2\, dx\, dz$$

Equation 2 which is an improved echo difference map with reduced tissue motion artifacts.

It is understood that one or more of the previously-described embodiments, expressions of embodiments, examples, methods, etc. can be combined with any one or more of the other previously-described embodiments, expressions of embodiments, examples, methods, etc. For example, and without limitation, any of the ultrasound transducers may be used with other methods of medical treatment, such as producing images to aid in tissue ablation by means of Radio Frequency (RF) and laser energy, various non-ablative ultrasound medical treatments, and various ultrasound imaging applications.

The foregoing description of several expressions of embodiments and methods of the invention has been presented for purposes of illustration. It is not intended to be exhaustive or to limit the present invention to the precise forms and procedures disclosed, and obviously many modifications and variations are possible in light of the above teaching. It is intended that the scope the invention be defined by the claims appended hereto.

What is claimed is:

1. A method for ultrasound imaging of anatomical tissue using an ultrasound transducer, comprising the steps of:
    a) positioning the ultrasound transducer relative to the anatomical tissue;
    b) receiving a time-varying first signal of a first imaging ultrasound wave which has been reflected from a location in the anatomical tissue during a first time period, the first imaging ultrasound wave being generated by the ultrasound transducer;
    c) receiving a time-varying second signal of a second imaging ultrasound wave which has been reflected from the location in the anatomical tissue at a later second time period following a discrete ultrasound medical treatment, the second imaging ultrasound wave being generated by the ultrasound transducer;
    d) subtracting the second signal from the first signal to derive a time-varying difference signal; and
    e) generating an indication from the difference signal, the indication showing the effect of the discrete ultrasound medical treatment in the location in the anatomical tissue.

2. The method of claim 1 wherein the first and second signals are received after the discrete ultrasound medical treatment has been completed.

3. The method of claim 1 wherein the first signal is received before the discrete ultrasound medical treatment, and the second signal is received after the discrete ultrasound medical treatment has been completed.

4. The method of claim 1, further comprising the step of processing the first and second signals.

5. The method of claim 4, further comprising the step of multiplying at least one of the first and second signals by a phase compensation function to reduce motion artifacts.

6. The method of claim 1, further comprising the step of scaling the difference signal.

7. The method of claim 6 wherein the difference signal is scaled by squaring the amplitude of the difference signal.

8. The method of claim 1, further comprising the step of spatially filtering the difference signal.

9. The method of claim 1, wherein the ultrasound medical treatment includes tissue ablation.

10. The method of claim 1, also including the steps a) through d) for different locations to image the anatomical tissue, wherein the image includes medically-treated locations and medically-untreated locations of the anatomical tissue.

11. The method of claim 1, further comprising the step of combining the difference signal image with a second image of the location in the anatomical tissue.

12. The method of claim 11 wherein the second image is generated using a B-Mode ultrasound scan.

13. A method for ultrasound imaging of anatomical tissue using an ultrasound transducer, comprising the steps of:
   a) positioning the ultrasound transducer relative to the anatomical tissue;
   b) receiving a time-varying first signal of a first imaging ultrasound wave which has been reflected from a location in the anatomical tissue during a first time period, the first imaging ultrasound wave being generated by the ultrasound transducer;
   c) receiving a time-varying second signal of a second imaging ultrasound wave which has been reflected from the location in the anatomical tissue at a later second time period following a discrete ultrasound medical treatment, the second imaging ultrasound wave being generated by the ultrasound transducer;
   d) processing the first and second signals;
   e) subtracting the second signal from the first signal to derive a time-varying difference signal;
   f) scaling the difference signal;
   g) spatially filtering the difference signal; and
   h) generating an indication from the difference signal, the indication showing the effect of the discrete ultrasound medical treatment in the location in the anatomical tissue.

14. The method of claim 13 wherein the first and second signals are received after the discrete ultrasound medical treatment has been completed.

15. The method of claim 13 wherein the first signal is received before the discrete ultrasound medical treatment and the second signal is received after the discrete ultrasound medical treatment.

16. A method for ultrasound imaging of anatomical tissue using an ultrasound transducer, comprising the steps of:
   a) positioning the ultrasound transducer relative to the anatomical tissue;
   b) receiving a first set of image frames comprising a plurality of time-varying imaging ultrasound wave signals which have been reflected from a location in the anatomical tissue during a first period of time;
   c) receiving a second set of image frames comprising a plurality of time-varying imaging ultrasound wave signals which have been reflected from the location in the anatomical tissue during a later second period of time following a discrete ultrasound medical treatment;
   d) subtracting the imaging ultrasound signals of the second set of image frames from the imaging ultrasound signals of the first set of image frames to derive a time-varying difference signal; and
   e) generating an indication from the difference signal, the indication showing the effect of the discrete ultrasound medical treatment in the location in the anatomical tissue.

17. The method of claim 16 wherein the first and second sets of image frames are received after the discrete ultrasound medical treatment has been completed.

18. The method of claim 16 wherein the first set of image frames is received before the discrete ultrasound medical treatment, and the second set of image frames is received after the discrete ultrasound medical treatment.

19. The method of claim 16, further comprising the step of processing the first and second sets of signals.

20. The method of claim 16, further comprising the step of scaling the difference signal.

21. The method of claim 20 wherein the difference signal is scaled by squaring the amplitude of the difference signal.

22. The method of claim 16, further comprising the step of spatially filtering

23. The method of claim 16, wherein the ultrasound medical treatment includes tissue ablation.

24. The method of claim 16, also including the steps a) through d) for different locations to image the anatomical tissue, wherein the image includes medically-treated locations and medically-untreated locations of the anatomical tissue.

25. A method for ultrasound imaging of anatomical tissue using an ultrasound transducer, comprising the steps of:
   a) positioning the ultrasound transducer relative to the anatomical tissue
   b) receiving a first set of image frames comprising a plurality of time-varying imaging ultrasound wave signals which have been reflected from a location in the anatomical tissue during a first period of time;
   c) receiving a second set of image frames comprising a plurality of time-varying imaging ultrasound wave signals which have been reflected from the location in the anatomical tissue during a later second period of time following a discrete ultrasound medical treatment;
   d) processing the first and second sets of signals;
   e) subtracting the imaging ultrasound signals of the second set of image frames from the imaging ultrasound signals of the first set of image frames to derive a time-varying difference signal;
   f) scaling the difference signal;
   g) spatially filtering the difference signal; and
   h) generating an indication from the difference signal, the indication showing the effect of the discrete ultrasound medical treatment in the location in the anatomical tissue.

26. The method of claim 25 wherein the first and second sets of image frames are received after the discrete ultrasound medical treatment has been completed.

27. The method of claim 25 wherein the first set of image frames is received before the discrete ultrasound medical treatment, and the second set of image frames is received after the discrete ultrasound medical treatment.

28. The method of claim 25 wherein the ultrasound medical treatment includes tissue ablation.

29. The method of claim 25, also including the steps a) through g) for different locations to image the anatomical tissue, wherein the image includes medically-treated locations and medically-untreated locations of the anatomical tissue.

30. A method for ultrasound imaging of anatomical tissue using an ultrasound transducer, comprising the steps of:
   a) positioning the ultrasound transducer relative to the anatomical tissue;
   b) providing a discrete ultrasound medical treatment to the anatomical tissue;
   c) receiving a set of image frames comprising a plurality of time-varying imaging ultrasound wave signals which have been reflected from a location in the anatomical tissue;

d) pairing together a plurality of image frames, each pair comprising a first image frame and a second image frame such that the second image frame has been reflected from a location in the anatomical tissue at a later time than the first image frame;

e) subtracting the signals of the second image frame from the signals of the first image frame, for each pair of image frames in the image frame set, to derive a set of time-varying difference signals;

f) using at least one difference signal to generate an indication showing the effect of the discrete ultrasound medical treatment in the location in the anatomical tissue; and g) repeating steps a) through e) until medical treatment is completed.

31. The method of claim 30, further comprising the steps of:

a) computing an average of the set of difference signals; and b) using the average of the set of difference signals to generate an indication showing the effect of the discrete ultrasound medical treatment in the location in the anatomical tissue.

32. The method of claim 31, further comprising the steps of:

a) cumulatively summing the averages of the set of difference signals; and b) using the cumulative sum of averages of the set of difference signals to generate an indication showing the effect of the discrete ultrasound medical treatment in the location in the anatomical tissue.

* * * * *

UNITED STATES PATENT AND TRADEMARK OFFICE
CERTIFICATE OF CORRECTION

| | | |
|---|---|---|
| PATENT NO. | : 7,846,096 B2 | Page 1 of 1 |
| APPLICATION NO. | : 10/721034 | |
| DATED | : December 7, 2010 | |
| INVENTOR(S) | : T. Douglas Mast et al. | |

It is certified that error appears in the above-identified patent and that said Letters Patent is hereby corrected as shown below:

Claim 25, Column 10, Line 6: After the word "filtering", add the words "the difference signal."

Signed and Sealed this
Twenty-fourth Day of April, 2012

David J. Kappos
*Director of the United States Patent and Trademark Office*